United States Patent
Sunakawa et al.

Patent Number: 6,140,131
Date of Patent: Oct. 31, 2000

[54] METHOD AND APPARATUS FOR DETECTING HEAVY METALS IN SILICON WAFER BULK WITH HIGH SENSITIVITY

[75] Inventors: Ken Sunakawa; Kiichiro Asako; Toko Yagi; Yoshinori Hayamizu, all of Annaka, Japan

[73] Assignee: Shin-Etsu Handotai Co., Ltd., Tokyo, Japan

[21] Appl. No.: 09/159,434

[22] Filed: Sep. 24, 1998

[30] Foreign Application Priority Data

Sep. 26, 1997 [JP] Japan ................................. 9-279670
Jan. 12, 1998 [JP] Japan ................................. 10-016370

[51] Int. Cl.$^7$ .................................................. G01N 21/64
[52] U.S. Cl. .............................. 436/72; 436/73; 436/80; 436/172; 436/177; 422/82.08
[58] Field of Search ........................ 436/72, 80, 73, 436/172, 177; 422/82.08; 250/306, 307

[56] References Cited

U.S. PATENT DOCUMENTS 3,632,438  1/1972  Carlson et al. .
4,912,528  3/1990  Hwang et al. ............................. 356/36
5,943,552  8/1999  Koveshnikov et al. ................... 438/17

OTHER PUBLICATIONS

Railkar, T.A. "Detection of Metal Induced Gap States in Silicon" Appl. Phys. Lett. vol. 66, No. 8, Feb. 20, 1995, pp. 974–975.

*Primary Examiner*—Jeffrey Snay
*Attorney, Agent, or Firm*—Hogan & Hartson, LLP

[57] ABSTRACT

The present invention is to provide a method and apparatus for detecting heavy metals within the bulk of a silicon wafer with high sensitivity. An electric field is applied to a surface of the silicon wafer in order to aggregate heavy metals existing within the bulk of the silicon wafer to the surface of the wafer or the vicinity thereof, and the heavy metals aggregated to the surface of the wafer or the vicinity of the surface are analyzed. The application of an electric field is performed through corona-discharge treatment of the surface of the wafer, or through application of voltage to the surface of the wafer via a contact or non-contact electrode. Alternatively, an x-ray beam is radiated onto the surface of the silicon wafer in order to aggregate heavy metals existing within the bulk of the silicon wafer to the surface of the wafer or the vicinity thereof, and the heavy metals aggregated to the surface of the wafer or the vicinity thereof are analyzed. The method and apparatus for detecting heavy metals are simple and do not require a pre-treatment such as heat treatment which would cause secondary contamination.

20 Claims, 7 Drawing Sheets

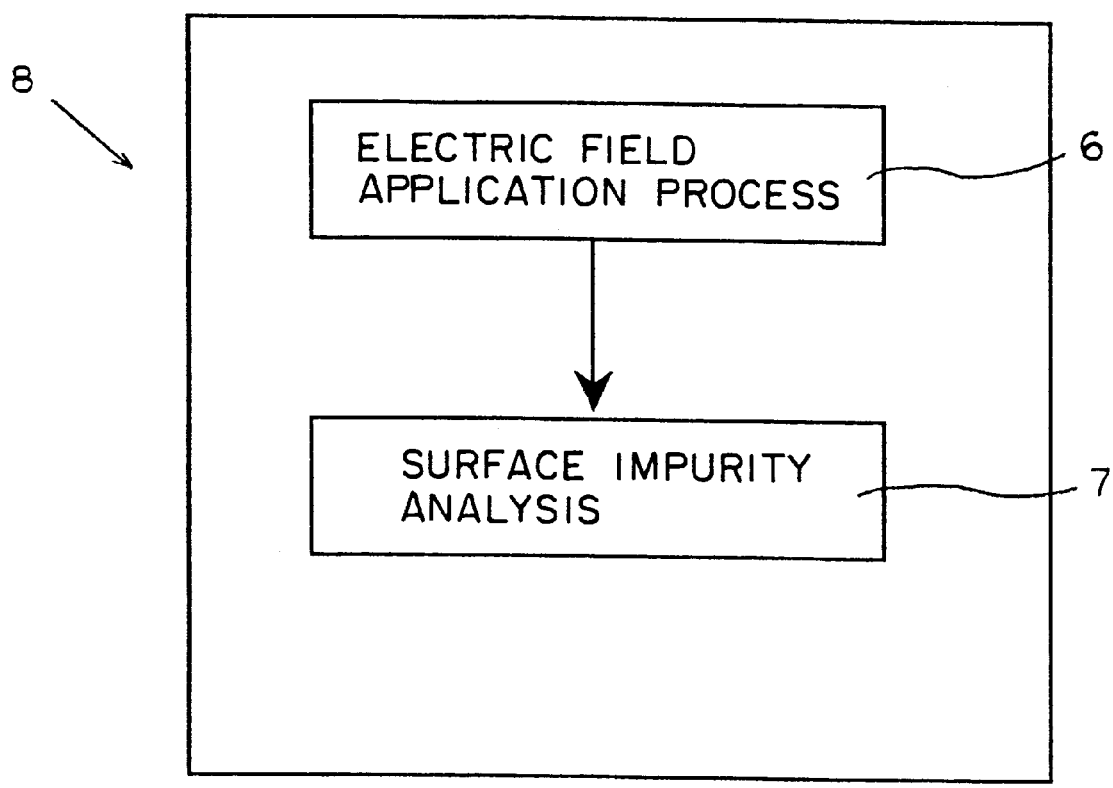

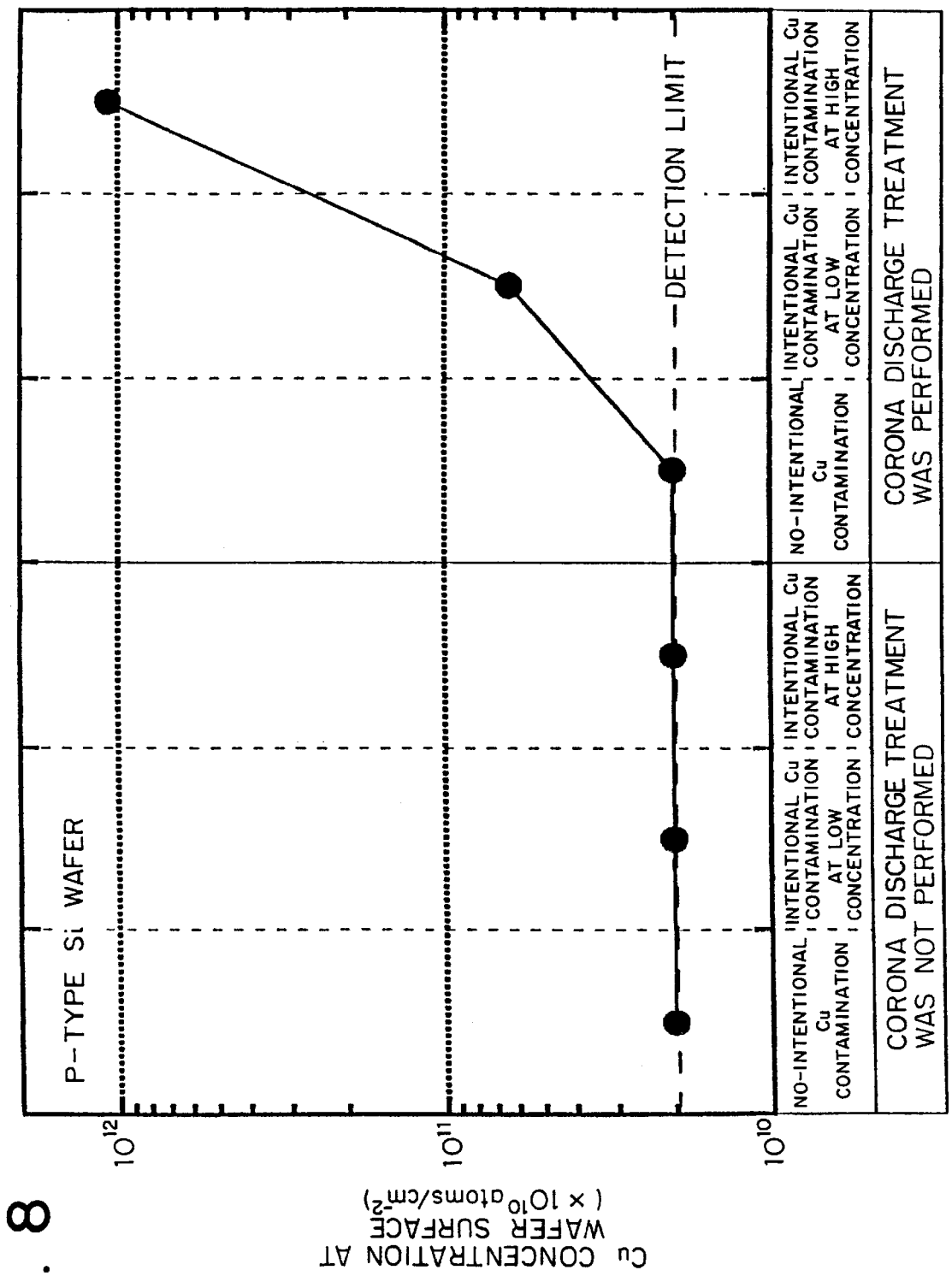

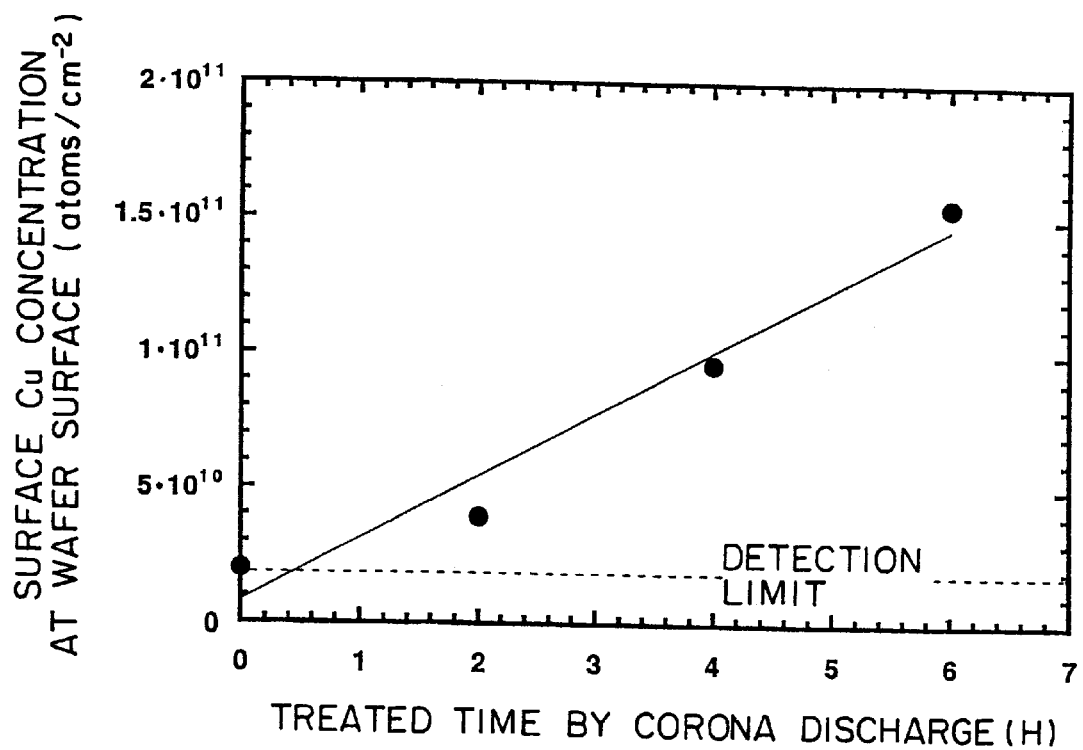

METHOD AND APPARATUS FOR DETECTING HEAVY METALS IN SILICON WAFER BULK WITH HIGH SENSITIVITY

BACKGROUND OF THE INVENTION

1. Field of the Invention

The present invention relates to analysis of heavy metals in a silicon wafer used for fabrication of semiconductor devices such as ICs and LSIs. More particularly, the present invention relates to a method and apparatus for detecting, with high sensitivity, heavy-metal impurities contained in a wafer bulk in the course of a process for manufacturing wafers or a process for fabricating semiconductor devices.

2. Description of the Related Art

During a process for manufacturing wafers or a process for fabricating semiconductor devices, heavy-metal impurities such as iron, copper, and nickel sometimes become contaminated into a wafer at the surface or in the bulk thereof. It is known that if such heavy-metal impurities exist in a region where semiconductor devices will operate, the electric characteristics of the semiconductor devices are degraded, and thus the operations thereof are hindered. Heavy-metal impurities existing at the surface of a wafer do not pose a great problem, because they can be directly analyzed and can be removed through cleaning. By contrast, heavy-metal impurities contained into the bulk of a wafer are difficult to analyze directly and are also difficult to remove. In addition, such heavy-metal impurities directly affect the characteristics of semiconductor devices. Therefore, highly sensitive detection of heavy-metal impurities within the bulk of a wafer is considerably important.

In order to analyze such heavy-metal impurities within the bulk of a wafer, there have conventionally been used chemical analysis, secondary-ion mass spectroscopy analysis, and the like.

Among them, chemical analysis is basically limited to analysis of samples in liquid form. Therefore, when a solid sample such as a semiconductor wafer is evaluated, for example, the surface of the wafer is chemically treated through use of HF solution, and the solution used for the treatment is collected and then subjected to atomic absorption spectroscopic analysis or ICP (Inductively Coupled Plasma) emission spectroscopic analysis in order to specify elements. Especially, in the field of semiconductors, there is used vapor phase decomposition/flameless atomic absorption spectroscopic analysis or vapor phase decomposition/ICP mass spectroscopic analysis. These methods have a disadvantage that the reliability of analyzed values are greatly affected by contaminants introduced into a sample during a pre-treatment process thereof. Further, much time and labor are needed to perform a pre-treatment process, and a person that performs the pre-treating must have a certain level of operational skill.

Also, there has been reported a technique in which a silicon wafer is subjected to heat treatment in order to aggregate impurities existing within the bulk to the surface or to the vicinity thereof, and the above-described chemical analysis is performed in order to analyze impurities within the bulk. However, this technique has a problem of contamination caused by the heat treatment.

Meanwhile, the secondary-ion mass spectroscopy analysis is a method for locally analyzing elements at high sensitivity and is used for analysis of impurities contained in a semiconductor in minute quantities. In this method, a beam of ions (primary ions) such as $O_2^+$, $Cs^+$, or $Ga^+$ having an energy of a few hundreds of eV to a few tens of keV or neutral particles such as those of Ar are radiated onto the surface of a sample. As a result, atoms at the surface of the sample are emitted into vacuum by means of sputtering. Among the sputtered particles, ionized particles (secondary ions) are extracted through application of an electric field and are subjected to mass spectroscopic analysis through use of a magnetic field and an RF electric field. Thus, the types and concentrations of elements contained on the surface of the sample are determined. This method is mainly used for analysis with respect to the depth direction of a sample, such as measurement of the dopant profile within a semiconductor material, and for analysis of behavior of impurities. However, an apparatus used in this method is expensive and maintenance of the apparatus is complicated and cumbersome because super-high vacuum is required.

Also, impurity analysis has been performed through use of total reflection x-ray fluorescence analysis. The total reflection x-ray fluorescence analysis is a method for non-destructive analysis of elements locally existing at the "surface" or at the "vicinity of the surface" of a sample in minute quantities. Therefore, by its very nature this method is inapplicable to detection of impurities within the bulk of a sample.

Although analysis of intra-bulk heavy metals through chemical analysis has a high detection sensitivity, this analysis requires a pre-treatment, which would contaminate a sample. In addition, since the analysis requires a destructive process such as dissolution of a sample, it is not simple and is time consuming.

The method in which analysis is performed after heat treatment is applied to a silicon wafer in order to aggregate heavy-metal impurities to the surface or to the vicinity thereof has a possibility of inducing secondary contamination caused by the heat treatment, so that true analysis values are difficult to obtain.

The analysis of intra-bulk heavy-metal impurities by use of the secondary-ion mass spectroscopy analysis has a disadvantage that the sensitivity changes depending on the types of elements, and therefore the setting and adjustment of measurement conditions are not easy. This method is also destructive.

The total reflection x-ray fluorescence analysis enables simple and non-destructive analysis of heavy-metal impurities contained in a silicon wafer. However, this method only analyzes the surface of a wafer and the vicinity thereof and cannot analyze the inside of the bulk. That is, the total reflection x-ray fluorescence analysis is applicable to a depth of only 100 Angstroms, and in ordinary analysis, evaluation is performed to a depth of 20–30 Angstroms.

If for some reason contamination caused by Cu, among heavy metals, occurs at the surface of a wafer, such contamination easily diffuses into the inside of the bulk. In this case, the analysis methods for analyzing or evaluating the surface of a wafer and the vicinity thereof cannot detect contamination even though the inside of the bulk is contaminated, or detects such contamination as being lower than the actual level. As described above, contamination caused by Cu is difficult to detect through an ordinary surface analysis. Therefore, even when a test for heavy metals is performed, contamination caused by heavy metals is overlooked, so that defectives may be generated is a subsequent device-fabrication process.

In general, when a method for analyzing the surface of a wafer is used, impurities existing at the surface of the wafer cannot be detected unless the concentration of impurities is greater than that corresponding to the detection limit of the analysis equipment. That is, even when contamination exists within the bulk, such contamination cannot be detected by the surface analysis alone. Especially, in the case of contamination caused by Cu, such contamination is sometimes not detected at the surface of a wafer even when the bulk of the wafer is contaminated to a level of $10^{15}$ atoms/cm$^3$.

SUMMARY OF THE INVENTION

In view of the foregoing, an object of the present invention is to provide a method and apparatus for detecting, with high sensitivity, heavy metals within the bulk of a wafer, and which is simple and does not require a pre-treatment such as heat treatment which would cause secondary contamination.

To achieve the above object, the present invention provides a method for detecting heavy metals within the bulk of a silicon wafer with high sensitivity, wherein an electric field is applied to a surface of a silicon wafer in order to aggregate heavy metals existing within the bulk of the silicon wafer to the surface or the vicinity thereof, and the heavy metals aggregated to the surface or the vicinity thereof are analyzed.

When an electric field is applied to a surface of a silicon wafer to thereby aggregate heavy metals contained within the bulk of the silicon wafer to the surface or the vicinity thereof, and analysis of heavy metals is then performed, there is substantially no fear of secondary contamination. Further, the surface to which heavy metals have been aggregated can be analyzed, and heavy metals can be detected simply and with high sensitivity.

The application of an electric field for the purpose of aggregating heavy metals existing within the bulk of a silicon wafer to the surface or the vicinity thereof may be performed through corona-discharge treatment of the surface of the silicon wafer, or through application of voltage to the surface of the silicon wafer via a contact or non-contact electrode.

In this case, without causing contamination of the silicon wafer, a strong electric field can be applied to the surface of the wafer quite simply, so that heavy metals can be efficiently aggregated to the surface of the wafer or to the vicinity thereof.

The present invention also provides a method for detecting, with high sensitivity, heavy metals within the bulk of a silicon wafer, wherein an x-ray beam is radiated onto a surface of the silicon wafer in order to aggregate heavy metals existing within the bulk of the silicon wafer to the surface or the vicinity thereof, and the heavy metals aggregated to the surface or the vicinity thereof are analyzed.

In this method, through radiation of an x-ray beam to a surface of a silicon wafer, heavy metals which are dispersed within the bulk of the silicon wafer and whose concentration is therefore below a detection limit of an analysis equipment are aggregated to the surface of the wafer or the vicinity thereof. Therefore, heavy metals can be detected simply, with high sensitivity, and without causing contamination.

The x-ray beam is preferably radiated onto the surface of the silicon wafer for 30 minutes or more. Also, the radiation of the x-ray beam is performed under the conditions that the voltage applied to an x-ray tube is 20 kV or greater, and the current flowing through the x-ray tube is 20 mA or more. Further, the angle of incidence of the x-ray beam is preferably set to 0.2° or less.

When the x-ray beam is radiated under the above-described conditions, heavy metals are sufficiently aggregated to the surface of the wafer by the action of the strong x-ray beam. Further, heavy metals located at deep positions can be aggregated to the surface of the wafer or the vicinity thereof by the radiation of the x-ray beam for a sufficiently long period of time. Moreover, in order to aggregate heavy metals to a shallow region, it is preferred that the angle of incidence of the x-ray beam is set to 0.2° or less. Accordingly, heavy metals within the wafer bulk can be detected with great sensitivity and can be analyzed quite simply.

When heavy metals existing within the bulk of the silicon wafer are aggregated to the surface of the wafer or the vicinity thereof, the silicon wafer is preferably heated to a temperature not greater than 300° C.

When the silicon wafer is heated to a low temperature, heavy metals diffuse quickly, and the heavy metals existing within the bulk of the silicon wafer are aggregated to the surface of the wafer or the vicinity thereof within a shorter period of time.

Preferably, the heavy metal aggregated layer at the surface or the vicinity thereof is analyzed through total reflection x-ray fluorescence analysis.

Since the total reflection x-ray fluorescence analysis is non-destructive, the heavy metal aggregated at the surface or to the vicinity thereof can be analyzed simply and accurately.

The heavy metal analyzed in accordance with the method of the present invention may be Cu.

Since Cu has a large diffusion coefficient within silicon and causes degradation of device characteristics, there is a strong demand for determining the degree of contamination caused by Cu.

In order to practice the above-described method of the present invention, an apparatus for analyzing heavy metals within the bulk of a silicon wafer comprises means for applying an electric field to the surface of the silicon wafer, and means for analyzing heavy metals at the surface of the wafer.

When the analysis apparatus comprises the combination of the means for applying an electric field to the surface of the silicon wafer, and the means for analyzing heavy metals at the surface of the wafer, heavy metals can be measured more simply and more quickly compared to the case where the application of an electric field and the analysis are performed separately and by individual apparatuses. In addition, since wafers do not have to be transported and stored, the problem of contamination does not occur, and highly precise measurement is enabled.

In the case, the application of an electric field to the surface of the silicon wafer may be performed through corona-discharge treatment of the surface of the silicon wafer, or through application of voltage to the surface of the silicon wafer via a contact or non-contact electrode.

Also, when an electric field is applied to the surface of the silicon wafer in order to aggregate heavy metals within the bulk of the silicon wafer to the surface of the wafer or the vicinity of the surface, the silicon wafer is preferably heated to a temperature not greater than 300° C.

It is preferred that the heavy metal aggregated layer at the surface is analyzed through total reflection x-ray fluorescence analysis.

In the present invention, analysis of heavy metals is performed, after heavy metals contained within the bulk of a silicon wafer are aggregated to the surface or the vicinity thereof through application of an electric field or radiation of an x-ray beam onto the surface of the silicon wafer. Accordingly, there is substantially no fear of secondary contamination such as that caused by heat treatment. Further, the surface to which heavy metals have been aggregated can be analyzed, and heavy metals can be detected simply and with high sensitivity.

BRIEF DESCRIPTION OF THE DRAWINGS

FIGS. 1A and 1B are graphs showing variation with time of the detected concentration of Cu within the bulk of a wafer when an x-ray beam is radiated in accordance with the present invention, wherein FIG. 1A shows a variation with time of the detected concentration of Cu in the case of a non-contaminated wafer serving as a reference, and FIG. 1B shows a variation with time of the detected concentration of Cu in the case of a wafer which was intentionally contaminated with copper and subjected to heat treatment such that the surface concentration became lower than a detection limit of total reflection x-ray fluorescence analysis;

FIG. 7 is a conceptual diagram of an apparatus according to the present invention;

FIG. 8 is a diagram showing the results of Example 1; and

FIG. 9 is a diagram showing the results of Example 2.

DESCRIPTION OF THE INVENTION AND PREFERRED EMBODIMENTS

Figure 1A:
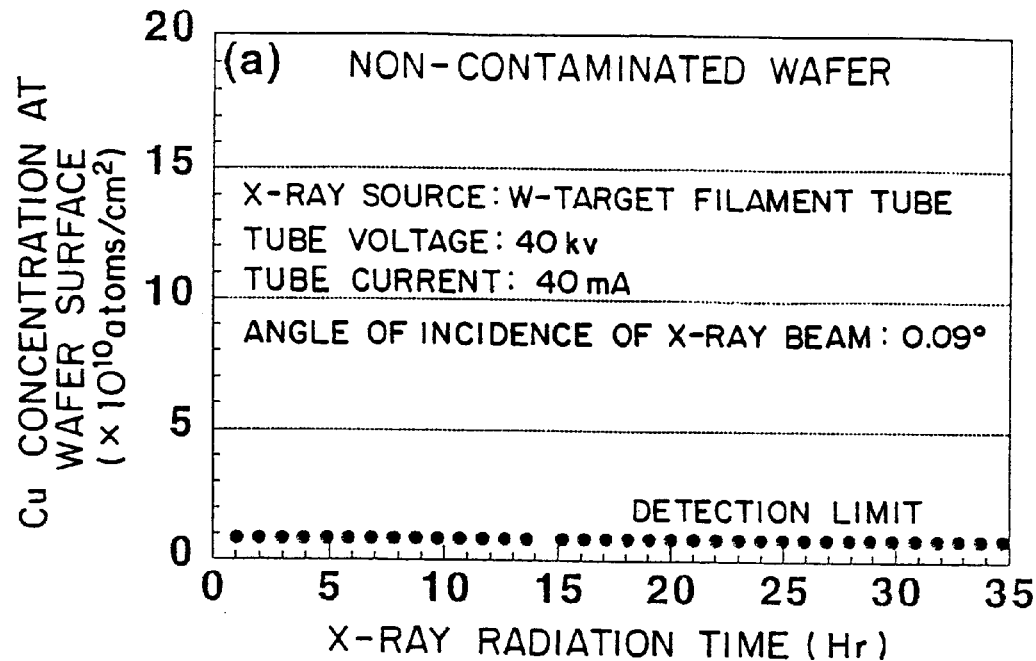

The present invention will now be described in further detail.

The inventors of the present invention carried out earnest studies on a method for detecting, with high sensitivity, heavy metal impurities within the bulk of a wafer which have been difficult to detect through use of conventional analysis method for a wafer surface, especially Cu, which has been more difficult to detect than other heavy metals, and found that heavy metals are aggregated to the surface of a wafer or to the vicinity thereof through radiation of an x-ray beam or application of en electric field onto the surface of the wafer and that analysis of the heavy metals can be performed through analysis of the heavy metal aggregated region. Based on this finding and through detailed investigations on various operating conditions, the present invention was completed.

First, a description will be given of the case where an x-ray beam is radiated onto the surface of a wafer.

The present invention is characterized in that an x-ray beam is radiated onto a mirror-surface of a silicon wafer at one point or over the entire surface thereof in order to aggregate heavy metals such as Cu existing within the bulk of the wafer to the surface or the vicinity thereof, and a region where the heavy metals are aggregated by the radiated x-lay beam is analyzed through use of a total reflection x-ray fluorescence analyzer or the like.

As the means for radiating the x-ray beam, there can be used, for example, a total reflection x-ray fluorescence analyzer that can use for an analysis of heavy metals or an x-ray diffraction apparatus that can radiate an x-ray beam of high intensity. Through radiation of an x-ray beam by use of these apparatuses, impurities are aggregated to a region near the surface (a region of 20–50 angstroms from the surface, or a region within 100 angstroms from the surface), which can be evaluated by means of total reflection x-ray fluorescence analysis or other analysis method.

When the total reflection x-ray fluorescence analyzer is used for radiation of x-rays, a subsequent analysis can be performed on the same apparatus, so that the analysis work is facilitated. In addition, since the depth of the region where heavy metals such as Cu aggregate corresponds to the depth of a region where analysis is performed, the analysis can be performed easily and accurately. However, in some cases, the intensity of the x-ray beam is insufficient because the total reflection x-ray fluorescence analyzer is designed for the purpose of analysis. In such a case, an apparatus for x-ray radiation may be provided separately from the total reflection x-ray fluorescence analyzer.

The present inventors found that radiating a high-intensity x-ray beam for a long period of time is considerably effective in aggregating heavy metals such as Cu existing within the bulk of a wafer to the surface or the vicinity thereof. That is, when impurities are analyzed through use of a total reflection x-ray fluorescence, an x-ray beam has conventionally been used. However, in the case where impurity analysis is performed through use of a total reflection x-ray fluorescence beam, the measurement time, i.e., the time for radiating an x-ray beam for analysis, has been 10–17 minutes at most. However, the radiation of the x-ray beam during such analysis does not cause heavy metals such as Cu existing within the bulk of a wafer to aggregate to the surface of the wafer. Therefore, such heavy metals cannot be detected unless impurities exist from the beginning at the surface of the wafer at a concentration above the detection limit.

However, when the impurity analysis was repeatedly performed through use of the total reflection x-ray fluorescence analysis, it gradually became possible to detect the impurities that had not been detected at the beginning of the analysis. The time period of x-ray radiation required for enabling detection of such impurities varies depending on the degree of contamination caused by heavy metals and the intensity of the x-ray beam. However, when the degree of contamination within the bulk of a wafer is high, such contamination can be detected through radiation of an x-ray beam for about 30 minutes even when the concentration of impurities existing at the surface of the wafer is below the detection limit. Further, even when the degree of contamination within the bulk of a wafer is low, such contamination becomes detectable when the radiation time of the x-ray beam is increased. This is the first time that the above-described phenomenon was actually observed.

The intensity of an x-ray beam that is radiated for the purpose of aggregation of heavy metals such as Cu is preferably made as strong as possible in consideration of the following phenomenon. In order to detect Cu in a silicon wafer (from which Cu at a concentration of $1.1 \times 10^{11}$ atoms/$cm^2$ had been detected by a different analysis method), an x-ray beam was radiated on the surface of the wafer through use of a vacuum sealed tube type (filament tube type) x-ray tube, which was operated at a tube voltage of 40 kV and a tube current of 40 mA. In this test, Cu in the silicon could be detected after radiation of the x-ray beam for about five hours. When the same measurement was performed in a state in which the intensity of the x-ray beam was made one-fourth its original value; i.e., the vacuum sealed tube type x-ray tube was operated at a tube voltage of 20 kV and a tube current of 20 mA, Cu was detected after more than 25 hours had elapsed. The results of this test demonstrate that as the intensity of the x-ray beam is increased, the speed of aggregation of heavy metals such as Cu increases, so that analysis can be performed within a shorter period of time.

The term "high sensitivity" used herein does not mean increased sensitivity of an apparatus used in analysis but means an improvement in the detection procedure in which an x-ray beam is radiated on a sample in order to aggregate impurities, thereby enabling detection of such impurities, which cannot detected through use of a conventional test method.

Through such an x-ray radiation process, the state in which impurities are aggregated in the surface layer of a wafer can be stably maintained for a long period of time. Therefore, even when impurities in the wafer are evaluated after the wafer is left for one week, the impurities can be detected. This means that even when an x-ray radiation apparatus which is stronger than the total reflection x-ray fluorescence analyzer is used to treat a wafer at a location and time different from those of the analysis, the analysis can be performed stably. Therefore, an x-ray apparatus that radiates a stronger x-ray beam, such as rotating anode type tube, can be employed.

The vacuum sealed tube type x-ray tube for radiating an x-ray beam for aggregation of heavy metals such as Cu is preferably operated at a tube voltage of 20 kV or more and a tube current of 20 mA or more. The operating conditions which determine strength of the x-ray beam vary depending on the type of the x-ray tube and setting of a monochromator. However, when the tube voltage and the tube current are below these values, the strength of the x-ray beam becomes insufficient, so that aggregation of heavy metals becomes impossible, or the time period of x-ray radiation required for enabling detection of impurities becomes excessively long as described above.

In principle, the angle of incidence of the x-ray beam is arbitrary. However, the angle of incidence is preferably equal to or less than 0.2°. If the angle of incidence exceeds 0.2°, the x-ray beam easily reaches a deep point within a wafer, with a possible result that heavy metals such as Cu are aggregated to a depth where impurities cannot be detected by surface analyzing methods such as a total reflection x-ray fluorescence analyzer. If such a phenomenon occurs, the analysis may become impossible to carry out with high sensitivity. Accordingly, the angle of incidence of the x-ray beam onto the wafer is preferably set to be equal to or less than 0.2°. The angle of incidence of the x-ray beam means an angle formed between the radiated x-ray and the surface of the wafer.

Even when the total reflection x-ray fluorescence analyzer is used as an analyzing method in order to analyze a aggregation layer, the angle of incidence of the x-ray beam is preferably set to be equal to or less than 0.2°. If the angle of incidence exceeds 0.2°, the x-ray beam easily reaches a deep point within a wafer, with a possible result that the background x-ray intensity increases and therefore impurities cannot be detected with high sensitivity.

The time of radiation of the x-ray beam onto a wafer can be freely determined in accordance with the depthwise distribution or profile of the concentration of heavy metals within the bulk of the wafer and strength of the x-ray beam. However, the x-ray radiation is preferably performed for 30 minutes or more while the x-ray tube is operated at a tube voltage of 20 kV or more and a tube current of 20 mA or more. If the time of x-ray radiation is shorter than 30 minutes, heavy metals cannot be sufficiently aggregated to the surface of the wafer even when the x-ray beam is of high intensity.

Subsequent to the above-described process for aggregating heavy metals to the surface of a wafer through radiation of an x-ray beam, the heavy metal impurities at the surface are analyzed through use of the total reflection x-ray fluorescence analyzer or the like.

Next, a description will be given of the case where an electric field is applied onto the surface of a wafer.

The method for detecting, with high sensitivity, heavy metals within the bulk of a silicon wafer according to the present invention is characterized in that an electric field is applied onto a surface of a silicon wafer in order to aggregate heavy metals existing within the bulk of the wafer to the surface or the vicinity thereof, and the aggregation layer where the heavy metals are aggregated is analyzed.

As described above, heavy metals existing within the bulk of a silicon wafer can be aggregated to the surface of the wafer or the vicinity thereof through application of an electric field to the surface of the wafer. Therefore, if the surface layer where aggregated heavy metals exist is analyzed, there is substantially no fear of occurrence of secondary contamination such as the case that heat treatment is applied. Further, since the surface can be analyzed, heavy metals can be detected easily with high sensitivity through use of a method, such as chemical analysis, secondary-ion mass spectroscopy analysis, or total reflection x-ray fluorescence analysis, which can be used to analyze the surface of a sample.

The reason why heavy metals existing within the bulk of a silicon wafer can be aggregated to the surface of the wafer or the vicinity thereof through application of an electric field to the surface of the wafer has not yet been found. However, Cu in a p-type silicon wafer is known to be positively electrified at 700° C. (D. Gilles, W. Schroter and W. Bergholz, Phys. Rev. B41 (1990) 5770). Therefore, if Cu and other heavy metals existing within a silicon wafer are in a positively electrified state at room temperature, Cu and other heavy metals are conceivably attracted and aggregated to the surface of a wafer or to the vicinity of the surface when a process for negatively electrifying the surface of the wafer is performed.

Figure 3:
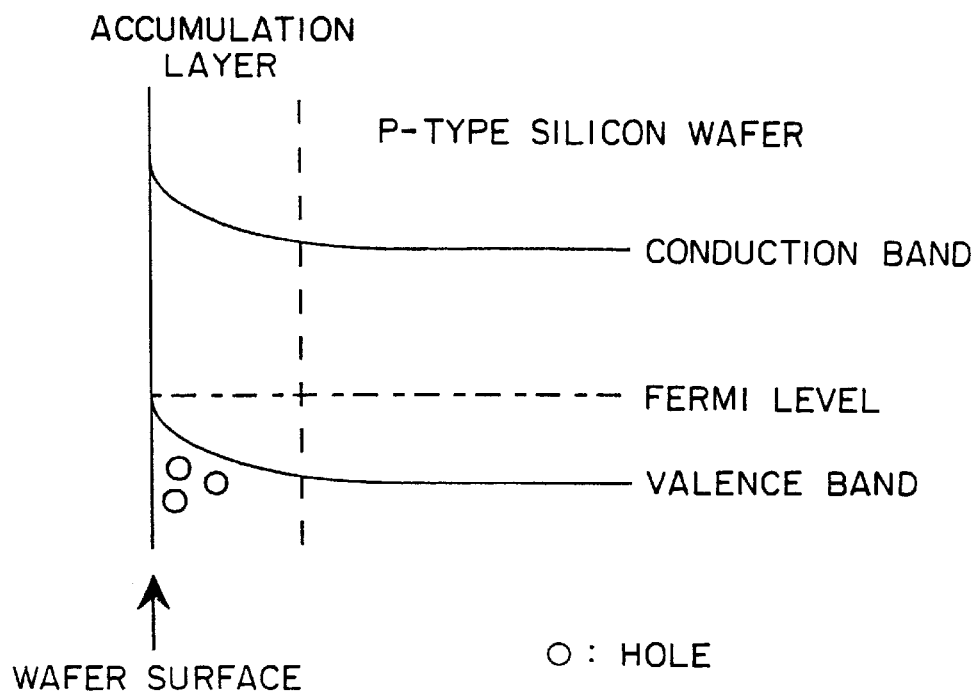
FIG. 3 is an explanatory diagram showing a band structure formed when a negative electric field is applied to a p-type silicon wafer.

For example, when a negative electric field is applied to a p-type silicon wafer, a band structure as shown in FIG. 3 is created. At this time, the surface layer is in an accumulation state, and therefore heavy metals that have positive charges within the bulk can be attracted to the vicinity of the surface due to the bending of the band.

In the present invention, any method can be used to apply an electric field to a surface of a silicon wafer in order to aggregate heavy metals existing within the bulk of the wafer to the surface or to the vicinity thereof. For example, the application of an electric field can be performed through a corona discharge treatment, or through application of voltage onto the surface of the silicon wafer via a contact type or non-contact-type electrode.

Insofar as an electric field is applied to the surface, heavy metals aggregate along the electric field. Therefore, the wafer surface is not necessarily required to be actually charged negatively. Accordingly, heavy metals can be aggregated to the surface by use of a method in which negative ions are poured and exist on the wafer surface by means of, for example, a corona discharge treatment.

The corona discharge treatment is a process in which a high voltage of 6–10 kV is applied to a metal wire having a diameter of about 100 microns to cause corona discharge and thereby treat the surface of an object such as a dielectric substance. The corona discharge treatment is widely used in the field of electrophotography.

Figure 4:
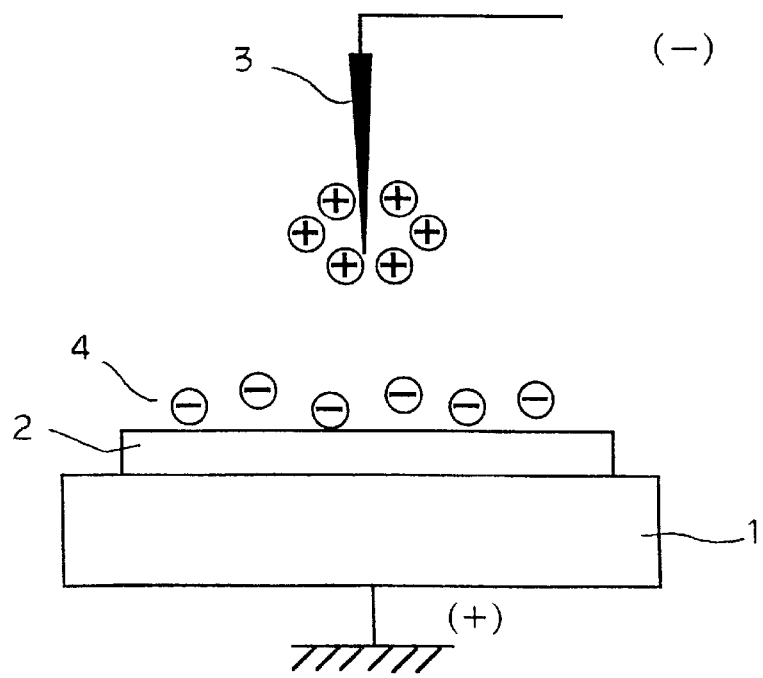
FIG. 4 is a conceptual diagram of a corona discharge apparatus used in the present invention.

This method uses a corona discharge apparatus as shown in FIG. 4. Specifically, a wafer such as a p-type silicon wafer 2 is placed on a stage 1, and a high voltage is applied between the stage 1 and a metal wire electrode 3, which is disposed above the silicon wafer 2 at the center thereof such that the metal wire electrode 3 is negatively charged. As a result, corona discharge is generated above the silicon wafer 2 so that negative ions 4 are poured onto the positively charged surface of the silicon wafer 2 on the stage 1.

In this way, an electric field is applied to the p-type silicon wafer, and positively charged heavy metals existing within the wafer bulk are attracted to the surface.

In this case, in order to effectively aggregate heavy metals to the wafer surface, the corona discharge treatment must be performed for four minutes or more at $1 \times 10^{10}$ q/cm²/sec.

Figure 5:
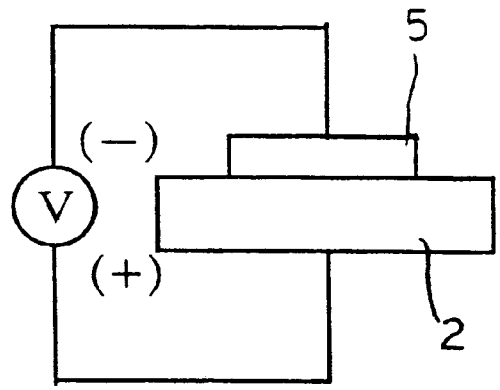
FIG. 5 is a conceptual diagram of an apparatus used in the present invention in which a voltage is applied to the surface of a silicon wafer through use of a contact-type electrode.
Figure 6:
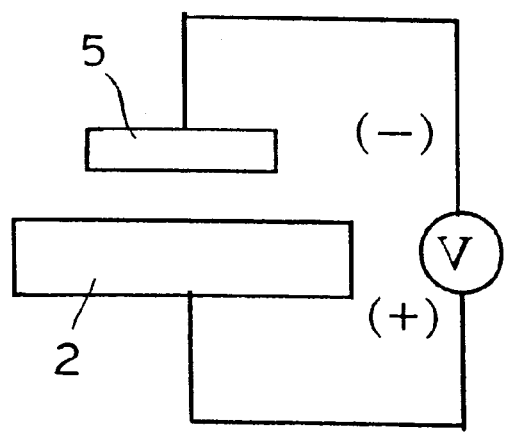
FIG. 6 is a conceptual diagram of an apparatus used in the present invention in which a voltage is applied to the surface of a silicon wafer through use of a non-contact-type electrode.

The method in which voltage is applied to the surface of a silicon wafer via a contact type or non-contact-type electrode can be carried out by use of apparatuses as shown in FIGS. 5 and 6.

FIG. 5 shows the case in which an electrode 5 is brought into contact with the surface of a silicon wafer 2. FIG. 6 shows the case in which the electrode 5 is disposed above the silicon wafer 2 at the approximate center thereof in a non-contacting state. When a high voltage is applied between the back surface of a p-type silicon wafer 2 and the electrode 5 such that the electrode 5 becomes negatively charged, positively electrified heavy metals existing within the bulk of the wafer are attracted to the surface.

In this case, the electrode may have any shape, and there may be used electrodes of various shapes such as a needle-like shape (probe) or a plate-like shape. However, the non-contact-type electrode is more preferred because it has no possibility of contaminating the wafer surface.

In the method utilizing corona discharge, the amount of heavy metals such as Cu attracted and aggregated to the surface layer can be further increased through an increase in the amount of negative ions poured onto the surface per each second and/or through an increase in the time period during which negative ions are poured onto the surface.

Further, in the method using an electrode, the amount of heavy metals such as Cu attracted and aggregated to the surface layer can be further increased through an increase in the applied voltage and/or through an increase in the time period of voltage application.

In the method utilizing corona discharge or in the method using an electrode, the bulk of a silicon wafer does not suffer secondary contamination caused by heavy metals as in the case where heat treatment is performed. Therefore, heavy metals can be simply and efficiently aggregated to the surface of a silicon wafer or to the vicinity thereof.

In the present invention, a silicon wafer is preferably heated to a temperature not greater than 300° C. when heavy metals existing within the bulk of the wafer are aggregated to the surface of the silicon wafer or to the vicinity thereof through radiation of an x-ray beam or application of an electric field by means of corona discharge or by use of an electrode, or the like.

When a silicon wafer is heated, heavy metals diffuse quickly, even when the extent of the heating is slight. Thus, heavy metals can be effectively aggregated to the surface of the wafer or to the vicinity thereof, and the aggregation of heavy metals to the surface or to the vicinity thereof can be completed within a short time. In addition, the amount of ions poured onto the surface of the wafer and the voltage applied to the surface of the wafer can be decreased, and the x-ray radiation time can be shortened.

The reason why the temperature for heating a silicon wafer is set to be not greater than 300° C. is that if the heating temperature is greater than 300° C., the silicon wafer would be contaminated, as, in effect, a new heat treatment would be performed. In the case of low temperature heating at a temperature not greater than 300° C., contamination is not caused by impurities from a heating source and other members.

In order to heat a silicon wafer to a temperature not greater than 300° C. when an electric field is applied to the surface of the wafer, a heater such as a heating wire is built into the stage 1 of the corona discharge apparatus shown in FIG. 4. A silicon wafer 2 placed on the stage 1 can be heated through heating of the stage 1. The manner of heating the silicon wafer is not limited thereto, and the wafer may be heated in a non-contacting manner by means of lamp heating, induction heating, or the like.

Heavy metals aggregated to the surface of a silicon wafer through x-ray radiation or electric field application can be detected with high sensitivity through use of a method, such as chemical analysis, secondary-ion mass spectroscopy analysis, or total reflection x-ray fluorescence analysis, which can be used to analyze heavy metals at the surface of the silicon wafer.

Among these methods, the total reflection x-ray fluorescence analysis is particularly advantageously used in the present invention.

This is because the total reflection x-ray fluorescence analysis is non-destructive, can easily and accurately analyze heavy metals aggregated to the surface of a silicon wafer or to the vicinity thereof, and does not contaminate the wafer during the analysis.

When a method utilizing application of an electric field is performed among the above-described methods of the present invention, an apparatus for electric field application and an apparatus for surface analysis are separately prepared in order to perform a process for electric field application and a process for surface analysis individually. However, as shown in FIG. 7, an electric field application apparatus 6 may be built into a surface analyzing apparatus 7 as a pre-processing apparatus to thereby constitute a highly sensitive detection apparatus 8 for detecting heavy metals within the bulk of a silicon wafer with high sensitivity.

That is, the apparatus for analyzing heavy metals within the bulk of a silicon wafer may be formed of a combination of means for applying an electric field to the surface of a silicon wafer and means for analyzing heavy metals at the surface of the wafer.

In this case, heavy metals can be measured more simply and more quickly compared to the case where the application of an electric field and the analysis are performed separately on individual apparatuses. In addition, since wafers do not have to be transported and stored, the problem of contamination does not occur, and highly precise measurement is enabled.

In this case, means for applying an electric field to the surface of a silicon wafer may be an apparatus shown in FIG. 4 in which the surface of the silicon wafer is treated by corona discharge. Alternatively, there may be used an apparatus in which voltage is applied to the surface of a silicon wafer a via contact type or non-contact-type electrode as shown in FIGS. 5 and 6.

Since these apparatuses can apply an electric field to the surface of a silicon wafer quite easily and are simple, they can be easily built into the analyzing apparatus.

In this case, there may be provided a heating mechanism for heating a silicon wafer to a temperature not greater than 300° C. when an electric field is applied to the surface of the wafer in order to aggregate heavy metals existing within the bulk of the wafer to the surface or to the vicinity thereof.

In the case of, for example, the corona discharge treatment shown in FIG. 4, the heating mechanism for heating a silicon wafer to a temperature not greater than 300° C. when an electric field is applied to the surface of the wafer may be of a resistance heating scheme in which a heater such as a heating wire is built into the stage 1, and the silicon wafer 2 placed on the stage 1 is heated through heating of the stage 1; a lamp heating scheme in which a radiation lamp disposed to surround the wafer 2 is caused to radiate radiation such as infrared radiation toward the wafer; or an induction heating scheme in which a voltage is applied to an induction coil such that the wafer is heated by means of eddy current.

The means for analyzing heavy metals at the surface layer of a wafer, which is combined with the above-described means for electric field application, may be a secondary-ion mass spectroscopy analyzer, a total reflection x-ray fluorescence analyzer, or the like. However, the total reflection x-ray fluorescence analyzer is particularly advantageously used in the present invention, because the total reflection x-ray fluorescence analysis can analyze a sample in a non-destructive manner.

EXAMPLES

Next, the present invention will be described more specifically by way of examples. However, the present invention is not limited to these examples.

Example 1

Two monocrystalline silicon wafers (diameter: 200 mm, thickness: 725 $\mu$m) were prepared, and an x-ray beam was radiated to the center of the mirror surface of each wafer for a long period of time. The x-ray radiation was performed through use of a total reflection x-ray fluorescence analyzer (TREX 610, product of Technos Corp.). The x-ray source was a tungsten target filament tube, and analysis was performed under conditions such that the tube voltage was 40 kV, the tube current was 40 mA, and the angle of incidence of the x-ray beam was 0.09 degrees.

One of the two monocrystalline wafers used in this example was a non-contaminated one, and the other was a contaminated one which had been contaminated through use of a Cu-containing solution and then subjected to heat treatment so that Cu was diffused into the bulk of the wafer and therefore the surface concentration of Cu was decreased to a level below the detection limit of the total reflection x-ray fluorescence analyzer.

That is, even in the case of the intentionally contaminated wafer, the contamination near the surface becomes impossible to detect if Cu is diffused by heat treatment. The detection limit of the total reflection x-ray fluorescence analyzer used in this example is $8.1 \times 10^9$ atoms/cm$^2$.

Figure 1B:
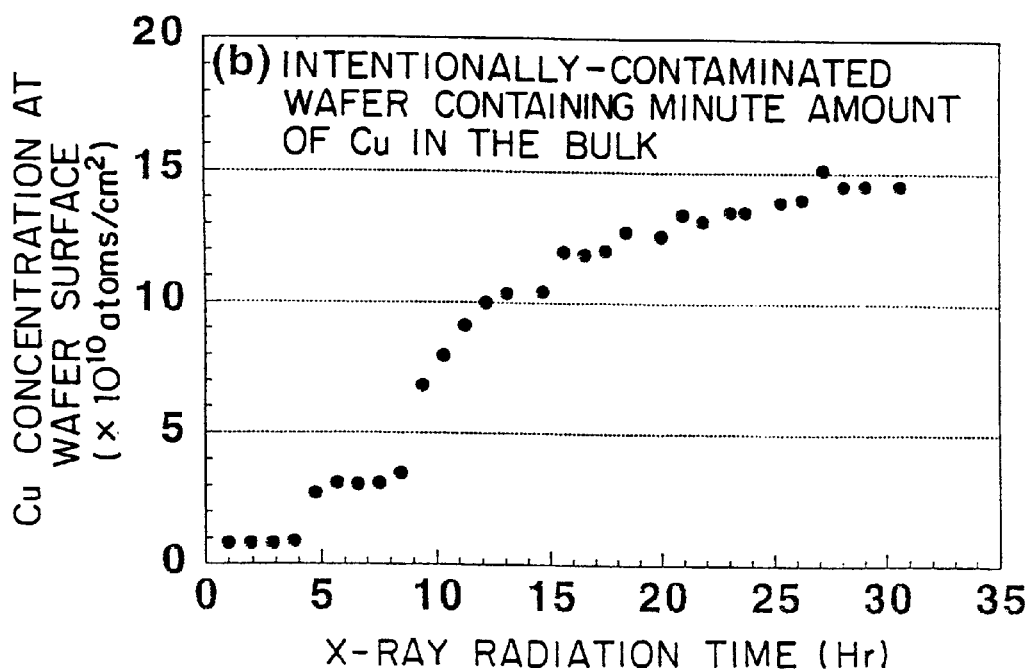

X-ray radiation was performed for the two kinds of wafers under the above-described conditions. The analysis of Cu aggregated to the surface was performed concurrently with the x-ray radiation on the total reflection x-ray fluorescence analyzer. The concentration of Cu at the wafer surface was measured every hour. FIGS. 1A and 1B each shows the variation with time of the concentration of Cu detected in this analysis.

FIG. 1A shows the variation with time of the concentration of Cu in the non-contaminated wafer. Even after x-ray radiation for 35 hours, the Cu concentration remains below the detection limit ($8.1 \times 10^9$ atoms/cm$^2$) as in the initial stage of the measurement.

FIG. 1B shows the variation with time of the concentration of Cu in the intentionally-contaminated wafer. The Cu concentration exceeds the detection limit after x-ray radiation for 5 hours, and becomes detectable through use of the total reflection x-ray fluorescence analyzer. Even after that, the detected Cu concentration increases with the radiation time.

Example 2

Figure 2:
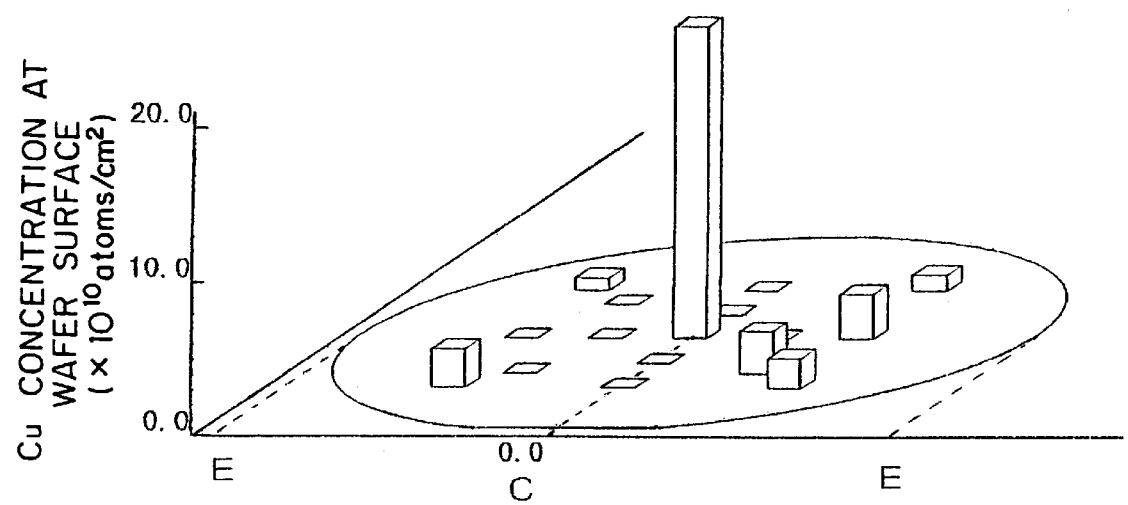
FIG. 2 is a graph showing the planar distribution of the detected Cu concentration after 60-hour radiation of x-ray beam at the central portion of a wafer which had been intentionally contaminated with copper and subjected to heat treatment such that the surface concentration became lower than a detection limit of total reflection x-ray fluorescence analysis.

FIG. 2 show the results of the measurement in which an x-ray beam (output voltage: 30 kV, current: 200 mA, angle of incidence: 0.090°) was radiated onto the center of the mirror surface of a wafer—which had been intentionally contaminated under the same conditions as those in Example 1—for 60 hours. Subsequently, the planar distribution of the Cu concentration was measured through use of the total reflection x-ray fluorescence analyzer. From FIG. 2, it is understood that Cu was detected only at the center portion of the wafer where the x-ray beam was radiated. This indicates that through the x-ray radiation for a long period of time, Cu was aggregated from the bulk of the wafer to the surface where the total reflection x-ray fluorescence analyzer can detect Cu.

Example 3

Six p-type monocrystalline silicon wafers (diameter: 150 mm, thickness: 625 $\mu$m) were prepared, and the Cu concentration at the wafer surface was measured after the wafer was treated in a manner described below. The measurement was performed through use of the total reflection x-ray fluorescence analyzer (TREX 610, product of Technos Corp.) The x-ray source was a tungsten target filament tube, and analysis was performed under conditions such that the tube voltage was 30 kV and the tube current was 200 mA.

Two of the six monocrystalline wafers used in this example were used as non-contaminated wafers. Two other wafers were contaminated through use of a solution containing Cu at a low concentration, and then subjected to heat treatment so that Cu was diffused into the bulk of the wafer. The remaining two wafers were contaminated through use of a solution containing Cu at a high concentration, and then subjected to heat treatment so that Cu was diffused into the bulk of the wafer.

One of two wafers in each group was measured through use of the total reflection x-ray fluorescence analyzer under the same conditions as described above.

The other wafer in each group was surface-treated by corona discharge. The apparatus as shown in FIG. 4 was used to perform corona discharge treatment at $1\times10^{10}$q/cm$^2$/sec. for 120 minutes while the wafer was heated at 250° C. After the treatment, the surface Cu concentration was measured on the total reflection x-ray fluorescence analyzer in the same manner as described above.

FIG. 8 shows the results of the measurement.

As is apparent from FIG. 8, not only in the case of the non-contaminated wafer but also in the case of the intentionally contaminated wafer, the contamination near the wafer surface falls below the detection limit when Cu is dispersed through heat treatment, and thus the contamination becomes impossible to detect by the total reflection x-ray fluorescence analyzer.

By contrast, when a contaminated wafer was surface-treated by corona discharge as in the present invention, Cu that has been diffused in the bulk and therefore becomes undetectable at the surface becomes detectable. That is, through application of an electric field on the surface of a wafer by means of corona discharge treatment, Cu dispersed in the bulk are attracted and aggregated to the surface.

Example 4

In order to further confirm that Cu is aggregated to the surface by the corona discharge treatment, the relationship between the time of the corona discharge treatment and the surface Cu concentration was studied.

A p-type monocrystalline silicon wafer (diameter: 150 mm, thickness: 625 μm) was prepared, contaminated through use of a solution containing Cu at a low concentration, and then subjected to heat treatment so that Cu was diffused into the bulk of the wafer.

The surface of this wafer was analyzed through use of the total reflection x-ray fluorescence analyzer in order to confirm that the surface Cu concentration was below the detection limit.

Subsequently, this wafer was surface-treated by means of corona discharge for 6 hours in total, and the surface Cu concentration was measured every two hours by use of the total reflection x-ray fluorescence analyzer. The corona discharge treatment was performed for two hours each time at $1\times10^{10}$q/cm$^2$/sec., while the wafer was heated at 20° C. The measurement was performed through use of the total reflection x-ray fluorescence analyzer (TREX 610, product of Technos Corp.) under the same conditions as in Example 1. That is, the x-ray source was a tungsten target filament tube, and analysis was performed under the conditions such that the tube voltage was 30 kV and the tube current was 200 mA.

FIG. 9 shows the results of the measurement.

As is apparent from FIG. 9, the concentration of Cu detected at the wafer surface increases as the time of the corona discharge treatment increases. This demonstrates that Cu diffused into the bulk is attracted to the surface by corona discharge.

The present invention is not limited to the above-described embodiments. The above-described embodiments are mere examples, and those having the substantially same structure as that described in the appended claims and providing the similar action and effects are included in the scope of the present invention.

In the above-described embodiments, a description has been given of the case where an x-ray beam is radiated on a wafer at one point thereof. However, the present invention is not limited to such a case, and an x-ray beam may be radiated on the wafer surface, depending on a purpose, at a plurality of points or over a certain region or the entire surface. In this case, an average value of the measured concentrations or the distribution of the concentration within the wafer surface is obtained.

Further, in the above-described embodiments, an x-ray beam is radiated onto a mirror surface (mirror-polished surface) of a wafer. However, the x-ray radiation for the purpose of aggregation of heavy metals such as Cu is not limited by the surface state of the wafer. The x-ray beam may be radiated onto a surface of any conditions such as a lapped surface, an etched surface, or a ground surface. However, in order to achieve sensitive analysis through use of a total reflection x-ray fluorescence, the x-ray beam is preferably radiated onto the mirror surface.

Further, the term "surface" used, for example, in the expression "heavy metals are aggregated to the surface of a silicon wafer through radiation of an x-ray beam or application of an electric field onto the surface of the wafer" encompasses not only the case where heavy metals are aggregated to the front surface of a silicon wafer but also the case where heavy metals are aggregated to the rear surface of the silicon wafer and the case where heavy metals are aggregated to the entire surface layer of the wafer.

What is claimed is:

1. A method for detecting heavy metals within the bulk of a silicon wafer with high sensitivity, said method comprising the steps of:

applying an electric field to a surface of a silicon wafer in order to aggregate heavy metals existing within the bulk of the silicon wafer to the surface of the wafer or the vicinity of the surface; and analyzing the heavy metals aggregated to the surface of the wafer or the vicinity of the surface.

2. A method for detecting heavy metals within the bulk of a silicon wafer with high sensitivity according to claim 1, wherein the application of an electric field for the purpose of aggregating heavy metals existing within the bulk of the silicon wafer to the surface or the vicinity thereof is performed through corona-discharge treatment of the surface of the wafer.

3. A method for detecting heavy metals within the bulk of a silicon wafer with high sensitivity according to claim 1, wherein the application of an electric field for the purpose of aggregating heavy metals existing within the bulk of the silicon wafer to the surface or the vicinity thereof is performed through application of voltage to the surface of the silicon wafer via a contact or non-contact electrode.

4. A method for detecting, with high sensitivity, heavy metals within the bulk of a silicon wafer, said method comprising the steps of:

radiating an x-ray beam onto a surface of a silicon wafer in order to aggregate heavy metals existing within the bulk of the silicon wafer to the surface of the wafer or the vicinity of the surface; and analyzing the heavy metals aggregated to the surface of the wafer or the vicinity of the surface.

5. A method for detecting heavy metals within the bulk of a silicon wafer with high sensitivity according to claim 4, wherein the x-ray beam is radiated onto the surface of the silicon wafer for 30 minutes or more.

6. A method for detecting heavy metals within the bulk of a silicon wafer with high sensitivity according to claim 4, wherein the radiation of the x-ray beam is performed under conditions that the voltage applied to an x-ray tube is 20 kV or greater, and the current flowing through the x-ray tube is 20 mA or more.

7. A method for detecting heavy metals within the bulk of a silicon wafer with high sensitivity according to claim 4, wherein the angle of incidence of the x-ray beam to a surface of the silicon wafer is preferably set to 0.2° or less.

8. A method for detecting heavy metals within the bulk of a silicon wafer with high sensitivity according to claim 1, wherein when heavy metals existing within the bulk of the silicon wafer are aggregated to the surface of the wafer or the vicinity thereof, the silicon wafer is heated to a temperature not greater than 300° C.

9. A method for detecting heavy metals within the bulk of a silicon wafer with high sensitivity according to claim 2, wherein when heavy metals existing within the bulk of the silicon wafer are aggregated to the surface of the wafer or the vicinity thereof, the silicon wafer is heated to a temperature not greater than 300° C.

10. A method for detecting heavy metals within the bulk of a silicon wafer with high sensitivity according to claim 3, wherein when heavy metals existing within the bulk of the silicon wafer are aggregated to the surface of the wafer or the vicinity thereof, the silicon wafer is heated to a temperature not greater than 300° C.

11. A method for detecting heavy metals within the bulk of a silicon wafer with high sensitivity according to claim 4, wherein when heavy metals existing within the bulk of the silicon wafer are aggregated to the surface of the wafer or the vicinity thereof, the silicon wafer is heated to a temperature not greater than 300° C.

12. A method for detecting heavy metals within the bulk of a silicon wafer with high sensitivity according to claim 1, wherein the heavy metals aggregated at the surface is analyzed through total reflection x-ray fluorescence analysis.

13. A method for detecting heavy metals within the bulk of a silicon wafer with high sensitivity according to claim 4, wherein the heavy metals aggregated at the surface is analyzed through total reflection x-ray fluorescence analysis.

14. A method for detecting heavy metals within the bulk of a silicon wafer with high sensitivity according to claim 1, wherein the heavy metal to be analyzed is Cu.

15. A method for detecting heavy metals within the bulk of a silicon wafer with high sensitivity according to claim 4, wherein the heavy metal to be analyzed is Cu.

16. An apparatus for detecting heavy metals within the bulk of a silicon wafer with high sensitivity, comprising:

means for applying an electric field to a surface of a silicon wafer in order to aggregate heavy metals existing within the bulk of the silicon wafer to the surface of the wafer or the vicinity of the surface; and means for analyzing heavy metals aggregated at the surface of the wafer or the vicinity of the surface.

17. An apparatus for detecting heavy metals within the bulk of a silicon wafer with high sensitivity according to claim 16, wherein the application of an electric field to the surface of the silicon wafer is performed through corona-discharge treatment of the surface of the wafer.

18. An apparatus for detecting heavy metals within the bulk of a silicon wafer with high sensitivity according to claim 16, wherein the application of an electric field to the surface of the silicon wafer is performed through application of voltage to the surface of the wafer via a contact or non-contact electrode.

19. An apparatus for detecting heavy metals within the bulk of a silicon wafer with high sensitivity according to claim 16, further comprising a heating mechanism for heating the silicon wafer to a temperature not greater than 300° C., when an electric field is applied to the surface of the wafer in order to aggregate heavy metals within the bulk of the silicon wafer to the surface of the wafer or the vicinity of the surface.

20. An apparatus for detecting heavy metals within the bulk of a silicon wafer with high sensitivity according to claim 16, the heavy metals aggregated at the surface of the wafer or the vicinity of the surface is analyzed through total reflection x-ray fluorescence analysis.

* * * * *